United States Patent
Ulrich et al.

(10) Patent No.: US 6,716,990 B2
(45) Date of Patent: Apr. 6, 2004

(54) PROCESS AND INTERMEDIATES FOR THE PREPARATION OF IMIDAZOPYRIDINES

(75) Inventors: Wolf-Rüdiger Ulrich, Constance (DE); Christian Scheufler, Engen-Neuhausen (DE); Thomas Fuchss, Constance (DE); Jörg Senn-Bilfinger, Constance (DE)

(73) Assignee: Altana Pharma AG, Constance (DE)

( * ) Notice: Subject to any disclaimer, the term of this patent is extended or adjusted under 35 U.S.C. 154(b) by 74 days.

(21) Appl. No.: 10/149,290

(22) PCT Filed: Jan. 11, 2001

(86) PCT No.: PCT/EP01/00261

§ 371 (c)(1),
(2), (4) Date: Jun. 11, 2002

(87) PCT Pub. No.: WO01/51486

PCT Pub. Date: Jul. 19, 2001

(65) Prior Publication Data

US 2003/0004358 A1 Jan. 2, 2003

(30) Foreign Application Priority Data

Jan. 13, 2000 (DE) .......................................... 100 01 037

(51) Int. Cl.[7] ..................... C07D 235/04; C07D 233/54
(52) U.S. Cl. .................................. 548/311.1; 548/303.1; 548/341.5
(58) Field of Search ........................... 548/311.1, 303.1, 548/341.5

(56) References Cited

U.S. PATENT DOCUMENTS 6,197,783 B1 * 3/2001 Senn-Bilfinger et al. .... 514/293

FOREIGN PATENT DOCUMENTS

| EP | 0033094 | 8/1981 |
|---|---|---|
| WO | 98/37080 | 8/1998 |
| WO | 98/42707 | 10/1998 |

* cited by examiner

*Primary Examiner*—T. A. Solola
*Assistant Examiner*—Ebenezer Sackey
(74) *Attorney, Agent, or Firm*—Nath & Associates PLLC; Gary M. Nath; Todd L. Juneau

(57) ABSTRACT

The invention relates to compounds of formula (2) in which R1, R2, R3 and R4 have the meanings indicated in the description, their preparation and their further reaction to give compounds of formula (1), in which $A_1$, $A_2$ and R4 have the meanings indicated in the description. The compounds of the formula (1) are valuable intermediates for the preparation of medicaments.

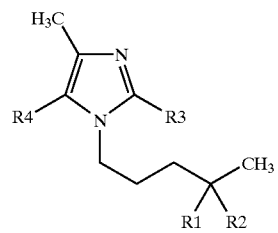

(1)

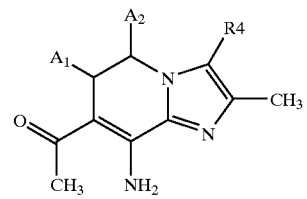

(2)

2 Claims, No Drawings

PROCESS AND INTERMEDIATES FOR THE PREPARATION OF IMIDAZOPYRIDINES

TECHNICAL FIELD

The invention relates to processes and intermediates for the preparation of imidazopyridines. These are needed as intermediates in the preparation of medicaments for the treatment of peptic ulcers.

PRIOR ART

The International Patent Application WO98/42707 describes 2,3-dimethyl-8-hydroxy-9-phenyl-7,8,9,10-tetrahydroimidazo[1,2-h][1,7]naphthyridin-7-ones and various processes for their preparation.

DESCRIPTION OF THE INVENTION

The invention relates to intermediates and processes for the preparation of compounds which can be employed for the preparation of the active compounds described in International Patent Application WO98/42707. In particular, the invention relates to compounds of the formula 1

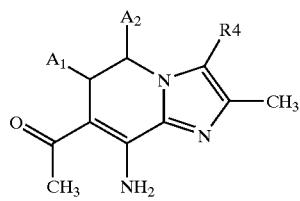

1 in which $A_1$ and $A_2$ are each hydrogen or together form a bond, R4 is hydrogen, methyl or trifluoro-methyl, and to their precursors and intermediates and processes for their preparation.

The invention relates in a first aspect to compounds of the formula 2

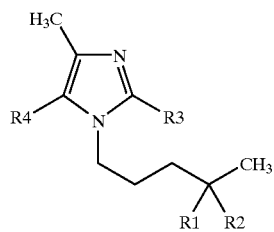

2 in which
R1 and R2 together are O (oxygen) or an ethylenedioxy radical (—O—CH$_2$—CH$_2$—O—),
R3 is hydrogen or cyano (CN),
R4 is hydrogen, methyl or trifluoromethyl
and their salts and their N-oxides.

Possible salts of compounds of the formula 2 are especially all acid addition salts. Particular mention may be made here of the salts of the customarily used inorganic and organic acids. Those suitable are water-soluble and water-insoluble acid addition salts with acids such as hydrochloric acid, hydrobromic acid, phosphoric acid, nitric acid, sulfuric acid, acetic acid or citric acid, where the acids can be employed in salt preparation—depending on whether a mono- or polybasic acid is concerned and depending on which salt is desired—in an equimolar quantitative ratio or one differing therefrom.

Compounds of the formula 2 in which R1 and R2 are an ethylenedioxy radical (—O—CH$_2$—CH$_2$—O—), R3 is hydrogen and R4 is hydrogen, methyl or trifluoromethyl, can be prepared in the form of their N-oxides, for example according to the following reaction scheme (scheme 1):

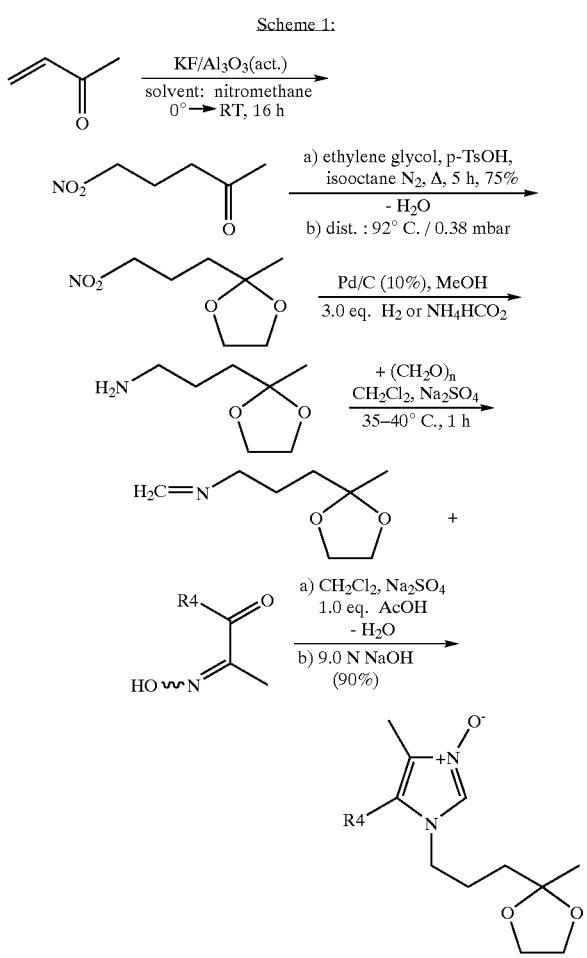

Starting from the compounds of the formula 2 obtained according to scheme 1, in which R1 and R2 are an ethylenedioxy radical (—O—CH$_2$—CH$_2$—O—), R3 is hydrogen, and R4 is hydrogen, methyl or trifluoromethyl, compounds of the formula 2 can be prepared in which R3 is cyano (CN), according to the process according to the invention outlined in scheme 2:

Scheme 2:

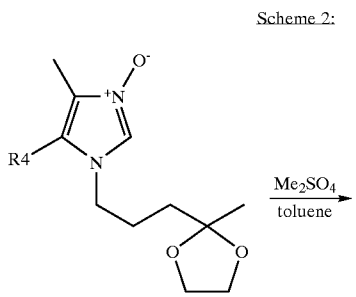

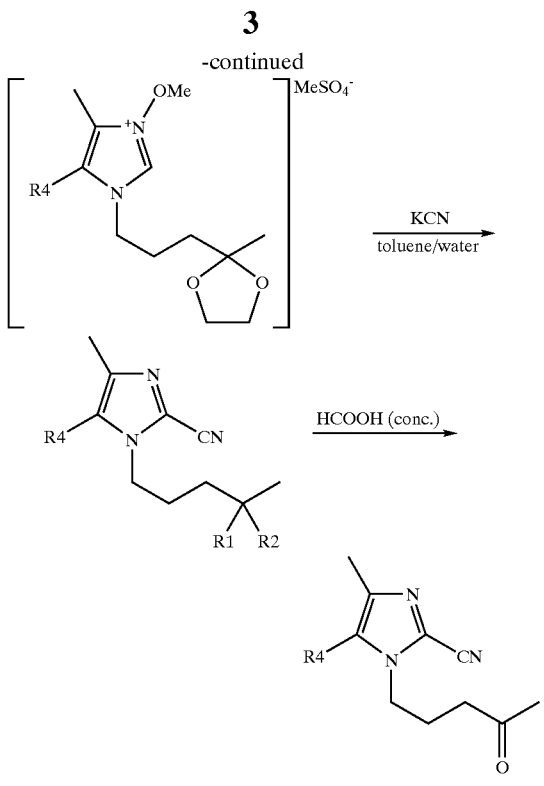

(in particular methyl iodide) or alkyl tosylates (such as methyl p-toluenesulfonate). The alkylation is carried out in inert solvents (e.g. toluene, halogenated hydrocarbons, such as dichloromethane, or ethers, such as diethyl ether) under customary conditions.

Suitable cyanides are preferably alkali metal cyanides, in particular sodium cyanide or potassium cyanide. Advantageously, the introduction of the cyano group is performed under catalytic conditions, in particular in the presence of tetrabutylammonium cyanide (TBACN). The reaction is preferably carried out in two-phase systems or in polar solvents, such as dimethylformamide (DMF).

The complete conversion of the ketal into the ketone which, if appropriate, is still necessary after introduction of the cyano group is preferably carried out under mild acidic conditions, for example in formic acid.

The invention further relates to the further reaction of the compounds of the formula 2, in which R1 and R2 together are O (oxygen), R3 is cyano (CN) and R4 is hydrogen, methyl or trifluoromethyl, to give compounds of the formula 1.

The further reaction consists in a cyclization step to give compounds of the formula 1, in which $A_1$ and $A_2$ are each hydrogen, to which is added, if desired, an oxidation step to give compounds of the formula 1, in which $A_1$ and $A_2$ together are a bonding dash. The cyclization and oxidation step can be illustrated by the following scheme 3:

Scheme 3:

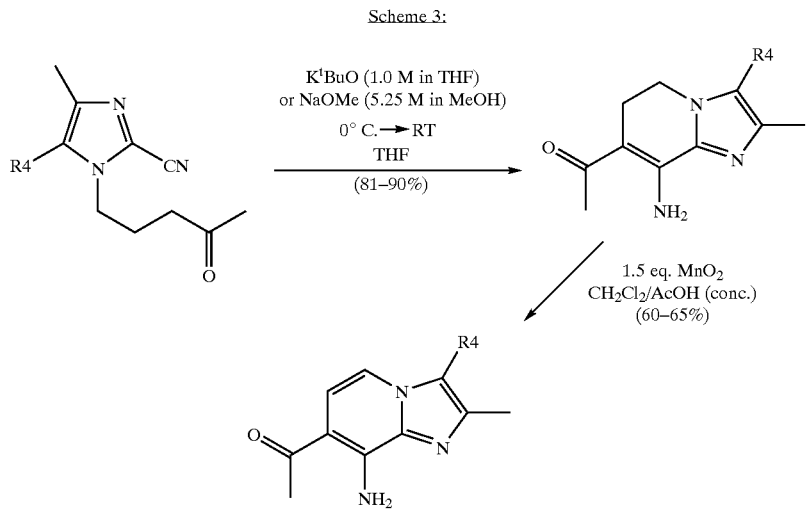

The invention thus relates in a further aspect to a process for the preparation of the compound of the formula 2 in which R1 and R2 together are O (oxygen), R3 is cyano (CN) and R4 is hydrogen, methyl or trifluoromethyl, and their salts. The process comprises first alkylating the N-oxide of the compound of the formula 2, in which R1 and R2 together are an ethylenedioxy radical (—O—CH$_2$—CH$_2$—O—), R3 is hydrogen and R4 is hydrogen, methyl or trifluoromethyl, then reacting it with a cyanide and finally working up in a suitable manner.

The person skilled in the art is familiar on the basis of his/her expert knowledge which alkylating agents can be employed and under what conditions alkylation must be carried out. Suitable alkylating agents are, for example, dialkyl sulfates (in particular dimethyl sulfate), alkyl halides For cyclization, the compound of the formula 2, in which R1 and R2 together are O (oxygen), R3 is cyano (CN) and R4 is hydrogen, methyl or trifluoromethyl, is reacted with a suitable deprotonating agent in an inert solvent. Suitable deprotonating agents which may be mentioned are, for example, alkali metal alkoxides, such as sodium methoxide or in particular potassium tert-butoxide. The oxidation (dehydrogenation) is carried out in a manner likewise known per se to the person skilled in the art using known dehydrogenating agents (such as sulfur or selenium) or in particular using known oxidants, preferably using manganese dioxide.

The following examples serve to explain the invention in greater detail without restricting it. Likewise, further compounds of the formulae 1 and 2, whose preparation is not described explicitly, can be prepared in an analogous manner or in a manner familiar per se to the person skilled in art using customary process techniques.

The abbreviation RT stands for room temperature, HV for high vacuum, h for hour(s) and min for minutes.

EXAMPLES 1. 5-Nitropentan-2-one a) Potassium fluoride (30.9 g) is dissolved in $H_2O$ (200 ml). Basic alumina (ICN Alumina B, Super 1; 150 g) is then carefully added in portions. The suspension obtained is homogenized with vigorous stirring and then concentrated to dryness in vacuo. The residue which remains is dried in a high vacuum at 100° C. for 14 h, activated $KF/Al_2O_3$ being obtained as a white powder (180 g) which is stored under dry $N_2$.

b) Nitromethane (2 800 ml) and methyl vinyl ketone (219 ml) are initially introduced and cooled to 0° C. in an ice bath. Activated $KF/Al_2O_3$ (30.8 g) is then added in portions and the ice bath is removed so that the reaction suspension slowly warms to RT. After about 15 min, a slightly yellow suspension is obtained, which is vigorously stirred for a further 18 h. For work-up, it is filtered off with suction through neutral alumina (ICN Alumina N, Super 1) and washed with a little dichloromethane, a colorless filtrate being obtained. The filtrate is concentrated to dryness in vacuo. A colorless oil (345 g) is obtained here, which consists of the title compound (306 g, 89%) and its dimers (38 g) in the ratio 8:1.

EI-MS: $_{m/z}$ (%)=149 (100) [$MNH_4^+$]

2. 5-Nitro-2,2-ethylenedioxypentane [2-methyl-2-(3-nitro-1-propyl)-1,3-dioxolane]

The crude product (130 g) obtained according to Example 1 is initially introduced and dissolved in isooctane (2,2-dimethyl-4-methylpentane, 740 ml) under an $N_2$ inert gas atmosphere. Ethylene glycol (276 ml) is then added, a two-phase system resulting. After addition of $_p$-toluenesulfonic acid monohydrate (1.85 g), the mixture is heated under reflux in a water separator (about 18 g of $H_2O$) for 5 h with vigorous stirring at an oil bath temperature of 120° C. After cooling to RT, saturated $NaHCO_3$ solution (250 ml) is added. After phase separation, the organic isooctane phase is washed twice with saturated NaCl solution (200 ml each). The organic phase is separated off and concentrated to dryness in vacuo. The combined aqueous phases are extracted twice with $CH_2Cl_2$ (300 ml each). The organic $CH_2Cl_2$ phase is dried over $Na_2SO_4$, filtered and concentrated to dryness in vacuo. The residual oil is combined with the residue of the above isooctane phase and distilled at 92° C. and 0.38 mbar. The title compound (130 g, 75%) is obtained here as a colorless oil.

EI-MS: $_{m/z}$ (%)=193 (100) [$MNH_4^+$], 176 (38) [$MH^+$]

3. 5-Amino-2,2-ethylenedioxypentane [2-(3-amino-1-propyl)-2-methyl-1,3-dioxolane]

5-Nitro-2,2-ethylenedioxypentane (103 g) is dissolved in methanol (2.0 l) and initially introduced into a hydrogenation flask. After the thorough flushing of the apparatus with $N_2$, 10% Pd/C (10 g) is added. Hydrogenation is then carried out at RT under normal conditions in a stream of $H_2$ for a total of 11 h with vigorous stirring. After the reaction is complete (TLC dichloromethane/methanol=9:1, staining reagent 1.0% strength ethanolic ninhydrin solution), the flask is flushed with $N_2$ and the mixture is filtered off with suction through kieselguhr. The colorless filtrate is concentrated to dryness at $T \leq 40°$ C. and $p \geq 30$ mbar, the title compound (85 g, quant.) first being obtained as a colorless oil, which solidifies to give a wax. TLC (dichloromethane/methanol=9:1), $R_f$=0.0 –0.22.

TSP-MS: $_{m/z}$ (%)=146 (100) [$MH^+$]

4. 3-$_N$-(2,2-Ethylenedioxypent-5-yl)-4,5-dimethylimidazole 1-$_N$-oxide

5-Amino-2,2-ethylenedioxypentane (138.5 g) is dissolved in $CH_2Cl_2$ (790 ml) and anhydrous $Na_2SO_4$ (90 g) is then added. Paraformaldehyde (33.5 g) is added in portions to the suspension with vigorous stirring. The reaction mixture is heated under reflux for 1 h in a water bath (T=45° C.). The suspension is then filtered off with suction, the solid is washed with a little $CH_2Cl_2$ and the filtrate containing the intermediate 5-amino-2,2 ethylenedioxy-$_N$-methylenepentane is concentrated to a volume of about 200 ml in vacuo. Glacial acetic acid (44.5 ml) and anhydrous $Na_2SO_4$ (75 g) are added to a solution of diacetyl monoxime (78.8 g) in $CH_2Cl_2$ (670 ml). The $CH_2Cl_2$ solution containing the methyleneimine is then slowly added dropwise to this suspension (heat effect) with cooling in a water bath. The reaction mixture is then stirred vigorously at RT for 14 h. After completion of the reaction [TLC dichloromethane/methanol=9:1, $R_f$ (title compound)=0.42–0.63, $_\lambda$=254 nm], 9.0 M NaOH (86.4 ml) is added and the mixture is stirred for 20 min until neutralization is complete. For drying, further anhydrous $Na_2SO_4$ (120 g) is added (clear reaction solution). The suspension is filtered off with suction and the filtrate is concentrated to dryness in vacuo, the title compound (a total of 221 g, about 90%) being obtained as a slightly yellow oil.

TSP-MS: $_{m/z}$ (%)=241 (100) [$MH^+$]

5. 2-Cyano-4,5-dimethyl-1-$_N$-(pentan-2-on-5-yl)imidazole a) 3-$_N$-(2,2-Ethylenedioxypent-5-yl)-4,5-dimethylimidazole 1-$_N$-oxide from Example 4 (200 g) is dissolved in toluene (320 ml). Dimethylsulfate (94 ml) is then added dropwise with cooling in a water bath (T=10° C.). The mixture is stirred overnight at RT for 20 h. A two-phase system is formed in the course of the reaction. The upper, toluene-containing phase contains no product and is decanted off. The residual oil is extracted twice by stirring with 250 ml of toluene each time and the wash phases are then decanted off. (TLC checks with dichloromethane/methanol=9:1).

b) After addition of a further 320 ml of toluene, potassium cyanide (59.6 g) which has been finely ground in a mortar is added in portions to the residue from a) with cooling in an ice bath. Water (200 ml) is slowly added dropwise with vigorous stirring and further cooling, a characteristic lightening in the color of the reaction suspension resulting. The mixture is gradually warmed to RT in the course of 3.5 h. After completion of the reaction (TLC toluene/acetone=4:1), the two-phase system is separated. The aqueous phase is extracted once with toluene (250 ml). The combined toluene phases are washed three times with semisaturated $NaHCO_3$ solution (200 ml each). The wash phases are combined and extracted once with toluene (200 ml). The combined organic phases are dried over $MgSO_4$, filtered off with suction and concentrated to dryness. 2-Cyano-3-$_N$-(2,2-ethylenedioxypent-5-yl)-4,5-dimethylimidazole and the title compound are obtained as crude products in the form of an oil (115 g, about 58%) in a ratio of about 3:1. TLC (toluene/acetone=4:1), $R_f$=0.33–0.39; $_\lambda$=254 nm.

c) The product mixture from b) (115 g) is treated with conc. formic acid (380 ml) for 6–7 h with cooling in an ice bath. After completion of the reaction (TLC toluene/acetone=4:1, $R_f$=0.33, $_\lambda$=254 nm), the mixture is concentrated to dryness in a high vacuum, then coevaporated a number of times with toluene. The residue which remains is dissolved in dichloromethane and carefully extracted three times with saturated $NaHCO_3$ solution. The organic phase is dried over $MgSO_4$, filtered off with suction and concentrated, the title compound [102 g, quant. with respect to b)] being obtained as a crude product in the form of an oil.

TSP-MS: $_{m/z}$ (%)=206 (100) [MH$^+$]

6. 7-Acetyl-8-amino-5,6-dihydro-2,3-dimethylimidazo[1,2-a]pyridine 102 g of 2-cyano-4,5-dimethyl-1-$_N$-(pentan-2-on-5-yl) imidazole from Example 5 are dissolved in tetrahydrofuran (1.2 l) under a dry N$_2$ atmosphere and cooled in an ice bath to T=0° C. Potassium tert-butoxide solution (1.0 M in THF, 640 ml) is then added dropwise over a period of about 15 min. After a further 15 min, the ice bath is removed so that the beige reaction suspension slowly warms to RT. It is then stirred vigorously for 2 h. After completion of the reaction (TLC toluene/acetone=4:1 and CH$_2$Cl$_2$/MeOH=9:1), saturated NH$_4$Cl solution (about 140 ml) is added until the cessation of the reaction and tetrahydrofuran is distilled off. The residue is then dissolved in dichloromethane and extracted twice with saturated NH$_4$Cl solution and once with saturated NaCl solution. The organic phase is dried (MgSO$_4$), filtered off with suction and concentrated to dryness in a high vacuum. The title compound is obtained here as a crude product in the form of an amorphous solid (86 g). The crude product is dissolved in ethanol (90 ml) at a temperature of about 85° C. The solution is then cooled in an ice bath and diethyl ether (180 ml) is added. The product phase is allowed to stand overnight at T=4° C. The precipitate of product is filtered off with suction, washed with a little cold diethyl ether and the filtercake is dried in a high vacuum. The mother liquor is concentrated to dryness, then taken up in the solvent mixture toluene/acetone=5:1 and treated with 5 times the amount of flash silica gel (Mallinckrodt-Baker, 30–60 μm). After filtration and removal of the solvent by distillation, precipitation is carried out again as described above. The title compound (55 g) is obtained as a pure substance in the form of a yellow-orange, amorphous solid, which is sensitive to photooxidation and is stored under N$_2$. TLC (CH$_2$Cl$_2$/MeOH=9:1), R$_f$=0.59; m.p.: 204° C. (decomposition).

7. 7-Acetyl-8-amino-2,3-dimethylimidazo[1,2-a]pyridine a) Activated manganese dioxide (MnO$_2$*): Powdered MnO$_2$ (250 g, Merck) is left in a high vacuum for 14 h at a temperature of 75° C. The product is stored under dry N$_2$ and employed as obtained for oxidative aromatization.

b) 7-Acetyl-8-amino-5,6-dihydro-2,3-dimethylimidazo[1,2-a]pyridine (136 g) is dissolved in glacial acetic acid (450 ml) and dichloromethane (110 ml) at RT. Activated MnO$_2$ (86 g, 1.5 equivalents) is then added in portions and the suspension obtained is stirred vigorously for 16 h. After completion of the reaction (TLC dichloromethane/methanol=9:1, R$_f$=0.67, $_\lambda$=254 nm, 366 nm), the solvents are removed by distillation by coevaporation with toluene a number of times. The residue is suspended in acetone, filtered off through kieselguhr, thoroughly subsequently washed with acetone and the filtrate is concentrated to dryness. 89 g of the crude product of the title compound are obtained here. The filtercake is then resuspended in dichloromethane and the solid is then filtered off with suction. By concentrating the filtrate, a further 21 g of crude product are obtained in this process as an amorphous solid. The combined crude products dissolved in dichloromethane are first extracted a number of times with saturated Na$_2$CO$_3$ solution, then with aqueous ethylenediamine tetraacetate solution (disodium salt, 250 mM). The aqueous phase is reextracted once with dichloromethane and the combined organic phases are dried over MgSO$_4$. After addition of 10% by volume of MeOH to the organic phase, it is filtered off with suction through flash silica gel (100 g, solvent-suspended) and subsequently washed with a little solvent. The filtrate is concentrated to dryness, the title compound being obtained as a beige, amorphous solid (84 g, 64%); m.p.: 188° C.

What is claimed is:

1. A compound of the formula 1

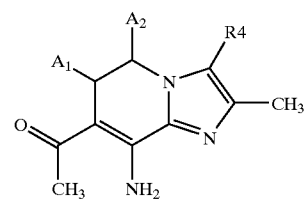

1 in which A$_1$ and A$_2$ are each hydrogen or together form a bond and R4 is hydrogen, methyl or trifluoromethyl, or its salts.

2. A process for preparing a compound of formula (I) according to claim 1, wherein A$_1$, A$_2$, and R$_4$ are as defined above which comprises cyclizing the compounds of formula (2) with deprotonation agent and, if desired, then oxidizing the compounds of formula (I) obtained to give compounds of formula (I) in which A$_1$ and A$_2$ together are a bonding dash,

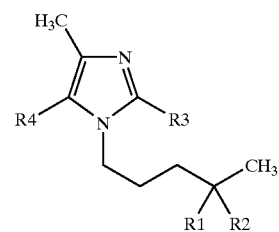

2 in which

R1 and R2 together are O (oxygen) or an ethylenedioxy radical (—O—CH$_2$—CH$_2$—O—), R3 is hydrogen or cyano (CN), R4 is hydrogen, methyl or trifluoromethyl or their salts and their N-oxides.

\* \* \* \* \*